United States Patent [19]

Brouwer Marius S. et al.

[11] Patent Number: 4,710,516
[45] Date of Patent: Dec. 1, 1987

[54] INSECTICIDAL AND ACARICIDAL COMPOSITION COMPRISING A BENZOYLUREA COMPOUND

[75] Inventors: Brouwer Marius S.; Arnoldus C. Grosscurt, both of Weesp, Netherlands

[73] Assignee: Duphar International Research B.V., Weesp, Netherlands

[21] Appl. No.: 932,296

[22] Filed: Nov. 19, 1986

Related U.S. Application Data

[63] Continuation-in-part of Ser. No. 572,143, Jan. 19, 1984, Pat. No. 4,665,235.

[30] Foreign Application Priority Data

Jan. 24, 1983 [NL] Netherlands .................... 8300238

[51] Int. Cl.$^4$ ............................................. A01N 47/28
[52] U.S. Cl. ..................................... 514/594; 514/586
[58] Field of Search .................................. 514/586, 594

[56] References Cited

U.S. PATENT DOCUMENTS 4,013,717 3/1977 Wellinga .............................. 564/44

FOREIGN PATENT DOCUMENTS 72438 2/1983 European Pat. Off. .
2926480 1/1980 Fed. Rep. of Germany .
2106499 4/1983 United Kingdom ................. 564/44

*Primary Examiner*—Allen J. Robinson
*Attorney, Agent, or Firm*—Stevens, Davis, Miller & Mosher

[57] ABSTRACT

The invention relates to an insecticidal and acaricidal composition comprising a benzoylurea compound of the general formula

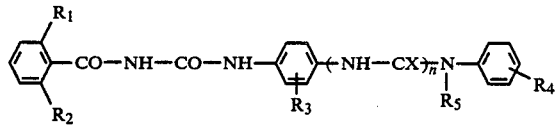

wherein
$R_1$ is a halogen atom,
$R_2$ is a hydrogen atom, a methoxy group or a halogen atom,
$R_3$ is a hydrogen atom or represents 1 or 2 substituents which are selected from the group consisting of halogen, methyl and trifluoromethyl,
$R_4$ is a hydrogen atom or represents 1–3 substituents which are selected from the group consisting of halogen, $C_1$–$C_4$ alkyl, $C_1$–$C_4$ alkoxy, $C_1$–$C_4$ haloalkyl and $C_1$–$C_4$ haloalkoxy,
X is an oxygen atom or a sulphur atom,
n is 0 or 1, and
$R_5$ is a hydrogen atom, a $C_1$–$C_6$ alkyl group, a $C_2$–$C_6$ alkenyl group or a $C_3$–$C_6$ cycloalkyl group, with the proviso, that, if n is 0 and $R_5$ is a hydrogen atom, $R_3$ is a hydrogen atom.

The composition may be used for the control of insects and/or mites in a dosage of 1 to 5,000 grams of active substance per hectare.

3 Claims, No Drawings

INSECTICIDAL AND ACARICIDAL COMPOSITION COMPRISING A BENZOYLUREA COMPOUND

REFERENCE TO RELATED APPLICATIONS

This application is a continuation in part of copending application Ser. No. 572,143, filed Jan. 19, 1984 now U.S. Pat. No. 4,665,235.

The invention relates to a composition having insecticidal and acaricidal activity and comprising a new benzoylurea compound as the active substance. The invention further relates to the use of said composition for controlling insects and/or mites.

N-Benzoyl-N'-phenylurea compounds having insecticidal activity are known from U.S. patent specification No. 4,013,717. In Chem. abstracts 91, 20141 (1979) benzoylurea compounds are described having both an insecticidal and an acaricidal activity, for example N-(2,6-difluorobenzoyl)-N'-(4-benzyloxphenyl)urea. This compound, however, proves to have no marked acaricidal activity in practically acceptable dosages.

In European patent application No. 0016729 N-(p-aminophenyl)-N'-benzoylurea are described, e.g. N-(2-chlorobenzoyl-N'-[3,5-dichloro-4-(N-methyl-N-allyl)aminophenyl]urea and N-2,6-difluorobenzoyl)-N'-[3,5-dichloro-4-(N-methyl-N-allyl)aminophenyl]urea. Also these compounds prove to have no acaricidal activity in practically acceptable dosages, as will be clear from the Examples. The same holds for N-(2-chlorobenzoyl)-N'-[4-(N-methyl-N-benzylimino)phenyl]- urea and N-(2,6-difluorobenzoyl)-N'-[4-(N-methyl-N-benzylimino)-phenyl]urea, known from U.S. patent specification No. 4,350,706.

It has surprisingly been found that the following benzoylurea compounds not only have strong insecticidal properties, but also show an interesting acaricidal activity, viz. benzoylurea compounds of the general formula:

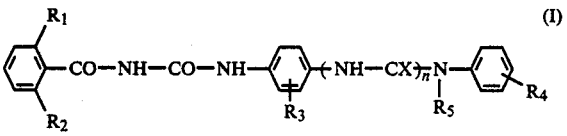

wherein $R_1$ is a halogen atom, $R_2$ is a hydrogen atom, a methoxy group or a halogen atom, $R_3$ is a hydrogen atom or represents 1 or 2 substituents which are selected from the group consisting of halogen, methyl and trifluoromethyl, $R_4$ is a hydrogen atom or represents 1-3 substituents which are selected from the group consisting of halogen, $C_1$–$C_4$ alkyl, $C_1$–$C_4$ alkoxy, $C_1$–$C_4$ haloalkyl and $C_1$–$C_4$ haloalkoxy, X is an oxygen atom or a sulphur atom, n is 0 or 1, and $R_5$ is a hydrogen atom, a $C_1$–$C_6$ alkyl group, a $C_2$–$C_6$ alkenyl group or a $C_3$–$C_6$ cycloalkyl group, with the proviso, that, if n is O and $R_5$ is a hydrogen atom, $R_3$ is a hydrogen atom. Of the above compounds generally those compounds prove to have a high acaricidal activity, which corresponding to the general formula

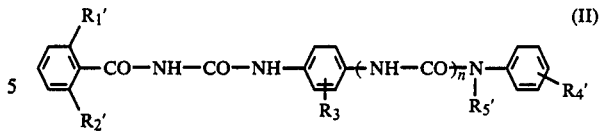

wherein $R_1'$ and $R_2'$ are both fluorine atoms, or wherein $R_1'$ is a chlorine atom and $R_2'$ is a hydrogen atom, $R_3$ is a hydrogen atom or represents 1 or 2 substituents which are selected from the group consisting of halogen, methyl and trifluoromethyl, $R_4$ is a hydrogen atom or represents 1-3 substituents which are selected from the group consisting of halogen, $C_1$–$C_4$ alkyl, $C_1$–$C_4$ haloalkyl and $C_1$–$C_4$ haloalkoxy, n is 0 or 1, and $R_5'$ is a hydrogen atom or a $C_2$–$C_5$ alkyl group, with the proviso, that, if n is O and $R_5'$ is a hydrogen atom, $R_3$ is a hydrogen atom.

If $R_3$ represents 1 or 2 halogen atoms, these halogen atoms are preferably selected from chlorine and fluor. Examples of new benzoylurea compound having insecticidal and acaricidal activity, to be used in compositions according to the invention are:

(1) N-(2-chlorobenzoyl)-N'-[4-{N-(4-chlorophenyl)-N-ethylamino}phenyl]urea, (2) N-(2,6-difluorobenzoyl)-N'-[4-{N-(4-chlorophenyl)-N-ethylamino}phenyl]urea, (3) N-(2-chlorobenzoyl)-N'-[4-{N-(4-chlorophenyl)-N-propylamino}phenyl]urea, (4) N-(2,6-difluorobenzoyl)-N'-[4-{N-(4-chlorophenyl)-N-propylamino}phenyl]urea, (5) N-(2,6-difluorobenzoyl)-N'-[3-chloro-4-{N-(4-chlorophenyl)-N-propylamino}phenyl]urea, (6) N-(2-chlorobenzoyl)-N'-[4-{N'-(4-chlorophenyl)-N'-isopropylureido}phenyl]urea, (7) N-(2-chlorobenzoyl)-N'-[4-{N'-(4-chlorophenyl)-N'-propylureido}phenyl]urea, (8) N-(2,6-difluorobenzoyl)-N'-[4-{N'-(4-chlorophenyl)-N'-propylureido}phenyl]urea, (9) N-(2-chlorobenzoyl)-N'-[4-(4-chloroanilino)phenyl]urea,

(10) N-(2-chlorobenzoyl)-N'-(4-anilinophenyl)urea,

(11) N-(2,6-difluorobenzoyl)-N'-[4-(2,4-dichloroanilino)phenyl]urea,

(12) N-(2-chlorobenzoyl)-N'-[3-chloro-4-{N-(4-chlorophenyl)-N-methylamino}phenyl]urea,

(13) N-(2,6-difluorobenzoyl)-N'-[3-chloro-4-{N-(4-chlorophenyl)-N-methylamino}phenyl]urea,

(14) N-(2-chlorobenzoyl)-N'-[4-{N-(4-chlorophenyl)-N-butylamino}phenyl]urea,

(15) N-(2,6-difluorobenzoyl)-N'-[4-{N-(4-chlorophenyl)-N-butylamino}phenyl]urea,

(16) N-(2-chlorobenzoyl)-N'-[4-{N-(4-trifluoromethylphenyl)-N-butylamino}phenyl]urea,

(17) N-(2,6-difluorobenzoyl)-N'-[4-{N-(4-trifluoromethylphenyl)-N-butylamino}phenyl]urea,

(18) N-(2,6-difluorobenzoyl)-N'-[4-(4-chloroanilino)-phenyl]urea,

(19) N-(2-chlorobenzoyl)-N'-[3,5-dimethyl-4-{N-(4-chlorophenyl)-N-propylamino}phenyl]urea,

(20) N-(2,6-difluorobenzoyl)-N'-[3,5-dimethyl-4-{N-(4-chlorophenyl)-N-propylamino}phenyl]urea,

(21) N-(2-chlorobenzoyl)-N'-[4-{N-(4-1,1,2,2-tetrafluoroethoxyphenyl)-N-ethoxyphenyl)-N-ethylamino}phenyl]urea,
(22) N-(2,6-difluorobenzoyl)-N'-[4-{N-(4-1,1,2,2-tetrafluoro-ethoxyphenyl)-N-propylamino}phenyl]urea,
(23) N-(2-chlorobenzoyl)-N'-[4-(4-1,1,2,2-tetrafluoroethoxyanilino)phenyl]urea,
(24) N-(2,6-difluorobenzoyl)-N'-[4-(4-1,1,2,2-tetrafluoroethoxyanilino)phenyl]urea,
(25) N-(2-chlorobenzoyl)-N'-[4-{N-(4-fluorophenyl)-N-ethylamino}phenyl]urea,
(26) N-(2,6-difluorobenzoyl)-N'-[4-{N-(4-fluorophenyl)-N-ethylamino}phenyl]urea,
(27) N-(2-chlorobenzoyl)-N-[4-(4-fluoroanilino)phenyl]urea,
(28) N-(2,6-difluorobenzoyl)-N'-[4-(4-fluoroanilino)phenyl[urea,
(29) N-(2,6-difluorobenzoyl)-N'-[3-chloro-4-{N-(4-1,1,2,2-tetrafluoroethoxyphenyl)-N-ethylamino}phenyl]urea,
(30) N-(2-chlorobenzoyl)-N'-[4-{N-(4-chlorophenyl)-N-isopropylamino}phenyl]urea,
(31) N-(2,6-difluorobenzoyl)-N'-[4-{N-(4-chlorophenyl)-N-isopropylamino}phenyl]urea,
(32) N-(2-chlorobenzoyl)-N'-[3-chloro-4-{N-(4-chlorophenyl)-N-ethylamino}phenyl]urea,
(33) N-2,6-difluorobenzoyl)-N'-[3-chloro-4-{N-(4-chlorophenyl)-N-ethylamino}phenyl]urea,
(34) N-(2-chlorobenzoyl)-N'-[4-{N'-(4-chlorophenyl)-N'-ethylureido}phenyl]urea,
(35) N-(2,6-difluorobenzoyl)-N'-[4-{N'-(4-chlorophenyl)-N'-isopropylureido}phenyl]urea,
(36) N-(2-chlorobenzoyl)-N'-[4-{N'-(4-chlorophenyl)-N'-butylureido}phenyl]urea,
(37) N-(2,6-difluorobenzoyl)-N'-[4-{N'-(4-chlorophenyl)-N'-butylureido}phenyl]urea,
(38) N-(2-chlorobenzoyl)-N'-[3-chloro-4-{N'-(4-chlorophenyl)-N'-butylureido}phenyl]urea,
(39) N-(2,6-difluorobenzoyl)-N'-[3-chloro-4-{N'-(4-chlorophenyl)-N'-butylureido}phenyl]urea,
(40) N-(2-chlorobenzoyl)-N'-[4-{N'-(4-trifluoromethyphenyl)-N'-butylureido}phenyl]urea,
(41) N-(2,6-difluorobenzoyl)-N'-[4-{N'-(4-trifluoromethylphenyl)-N'-butylureido}phenyl]urea,
(42) N-(2-chlorobenzoyl)-N'-[4-{N'-(4-methylphenyl)-N'-butylureido}phenyl]urea,
(43) N-(2,6-difluorobenzoyl)-N'-[4-{N'-(4-methylphenyl)-N'-butylureido}phenyl]urea,
(44) N-(2-chlorobenzoyl)-N'-[3-chloro-4-{N'-(4-methylphenyl)-N'-butylureido}phenyl]urea,
(45) N-(2,6-difluorobenzoyl)-N'-[3-chloro-4-{N'-(4-methylphenyl)-N'-butylureido}phenyl]urea,
(46) N-(2-chlorobenzoyl)-N'-[4-{N'-(4-1,1,2,2-tetrafluoroethoxyphenyl)-N'-butylureido}phenyl]urea,
(47) N-(2,6-difluorobenzoyl)-N'-[4-{N'-(4-1,1,2,2-tetrafluoroethoxyphenyl)-N'-butylureido}phenyl]urea,
(48) N-(2-chlorobenzoyl)-N'-[4-{N'-(4-1,1,2,2-tetrafluoroethoxyphenyl)-N'-propylureido}phenyl]urea,
(49) N-(2,6-difluorobenzoyl)-N'-[4-{N'-(4-1,1,2,2-tetrafluoroethoxyphenyl)-N'-propylureido}phenyl]urea,
(50) N-(2-chlorobenzoyl)-N'-[4-{N'-(4-chlorophenyl)-N'-isobutylureido}phenyl]urea,
(51) N-(2,6-difluorobenzoyl)-N'-[4-{N'-(chlorophenyl)-N'-isobutylureido}phenyl]urea,
(52) N-(2-chlorobenzoyl)-N'-[4-{N'-(4-chlorophenyl)-N'-hexylureido}phenyl]urea,
(53) N-(2,6-difluorobenzoyl)-N'-[4-{N'-(4-chlorophenyl)-N'-hexylureido}phenyl]urea,
(54) N-(2-chlorobenzoyl)-N'-[4-{N'-(4-chlorophenyl)-N'-pentylureido}phenyl]urea,
(55) N-(2,6-difluorobenzoyl)-N'-[4-}N'-(4-chlorophenyl)-N'-pentylureido}phenyl]urea,
(56) N-(2-chlorobenzoyl)-N'-[4-{N'-(2,6-dichlorophenyl)-N'-propylureido}phenyl]urea,
(57) N-(2,6-difluorobenzoyl)-N'-[4-{N'-(2,6-dichlorophenyl)-N'-propylureido}phenyl]urea,
(58) N-(2-chlorobenzoyl)-N'-[4-{N'-(3,4-dimethylphenyl)-N'-propylureido}phenyl]urea,
(59) N-(2,6-difluorobenzoyl)-N'-[4-{N'-(3,4-dimethylphenyl)-N'-propylureido}phenyl]urea,
(60) N-(2-chlorobenzoyl)-N'-[4-{N'-(4-fluorophenyl)-N'-propylureido}phenyl]urea,
(61) N-(2,6-difluorobenzoyl)-N'-[4-{N'-(4-fluorophenyl)-N'-propylureido}phenyl]urea,
(62) N-(2,6-difluorobenzoyl)-N'-[3-chloro-4-{N'-(4-chlorophenyl)-N'-propylureido}phenyl]urea,
(63) N-(2-chlorobenzoyl)-N'-[3-methyl-4-{N'-(4-chlorophenyl)-N'-propylureido}phenyl]urea,
(64) N-(2,6-difluorobenzoyl)-N'-[3-methyl-4-{N'-(4-chlorophenyl)-N'-propylureido}phenyl]urea,
(65) N-(2-chlorobenzoyl)-N'-[4-{N'-chlorophenyl)-N'-allylureido}phenyl]urea,
(66) N-(2,6-difluorobenzoyl)-N'-[4-{N'-(4-chlorophenyl)-N'-allylureido}phenyl]urea,
(67) N-2,6-difluorobenzoyl)-N'-[2-fluoro-4-{N'-(4-chlorophenyl)-N'-isopropylureido}phenyl]urea,
(68) N-(2,6-difluorobenzoyl)-N'-[3-chloro-4-{N'-(4-chlorophenyl)-N'-propylureido}phenyl]urea,
(69) N-(2-chloro-6-methoxybenzoyl)-N'-[4-{N'-(4-chlorophenyl)-N'-propylureido}phenyl]urea,
(70) N-(2-chlorobenzoyl)-N'-[3-chloro-4-{N'-(4-chlorophenyl)-N'-propylthioureido}phenyl]urea,
(71) N-(2-chlorobenzoyl)-N'-[3,5-dimethyl-4-{N'-(4-chlorophenyl)-N'-propylureido}phenyl]urea,
(72) N-(2,6-difluorobenzoyl)-N'-[3,5-dimethyl-4-{N'-(4-chlorophenyl)-N'-propylureido}phenyl]urea,
(73) N-(2-chlorobenzoyl)-N'-[3-trifluoromethyl-4-{N'-(4-chlorophenyl)-N'-propylureido}phenyl]urea, and
(74) N-(2,6-difluorobenzoyl)-N'-[3-trifluoromethyl-4-{N'(4-chlorophenyl)-N'-propylureido}phenyl]urea.

The compositions according to the invention may be used for the control of mites and insects in agriculture and horticulture, in forests and in surface water, as well as for the protection of textile against attack by, for example, moths and carpet beetles, against mites and insects in stocks, for example, in stored cereals, and against mites and insects in the veterinary and medical-hygienic sectors.

The compositions according to the invention may also be used for the control of insects living in the manure of warm-blooded animals, such as cows, pigs and hens. For this application the active compounds can be administered orally to the animals, for example, mixed through the food, so that they land in the manure after some time ("through-feeding").

The compounds to be used in compositions according to the invention are particularly active against larvae and eggs of mites and insects. In principle, the compounds may be used against all insects mentioned in Pestic. Sci. 9, 373–386 (1978).

For practical pesticidal application the active substances are usually processed into compositions. In such compositions the active substance is mixed with solid carrier material or dissolved or dispersed in liquid carrier material, if desired in combination with auxiliary substances, for example, emulsufiers, wetting agents, dispersible agents and stabilizers.

Examples of compositions according to the invention are aqueous solutions and dispersions, oily solutions and oily dispersions, solutions in organic solvents, pastes, dusting powders, dispersible powders, miscible oils, granules, pellets, invert emulsions, aerosol compositions and fumigating candles.

Dispersible powders, pastes and miscible oils are compositions in concentrate form which are diluted prior to or during use.

The invert emulsions and solutions in organic solvents are mainly used in air application, namely when large areas are treated with a comparatively small quantity of composition. The invert emulsion can be prepared shortly before or even during spraying in the spraying apparatus by emulsifying water in an oily solution or an oily dispersion of the active substance. The solutions of the active substance in organic solvents may be provided with a phytotoxicity-reducing substance, for example, wool fat, wool fatty acid or wool fatty alcohol.

A few forms of composition will be described in more detail hereinafter by way of example.

Granular compositions are prepared by taking up, for example, the active substance in a solvent or dispersing it in a diluent and impregnating the resulting solution/suspension, if desired in the presence of a binder, on granular carrier material, for example porous granules (for example pumice and attaclay), mineral non-porous granules (sand or ground marl), organic granules (for example, dried coffee grounds, cut tobacco stems or ground corncobs). A granular composition can also be prepared by compressing the active substance together with powered minerals in the presence of lubricants and binders and disintegrating the compressed product to the desired grain size and sieving it. Granular compositions can be prepared in a different manner by mixing the active substance in powder form with powdered fillers, and glomulating the mixture then with liquid to the desired particle size.

Dusting powders can be obtained by intimately mixing the active substance with an inert solid powdered carrier material, for example, talcum.

Dispersible powders are prepared by mixing 10 to 80 parts by weight of a solid inert carrier, for example kaolin, dolomite, gypsum, chalk, bentonite, attapulgite, colloidal $SiO_2$ or mixtures of these and similar substances, with 10 to 80 parts by weight of the active substance, 1 to 5 parts by weight or a dispersing agent, for example the lignine sulphonates or alkylnaphthalene sulphonates known for this purpose, preferably also 0.5 to 5 parts by weight of a wetting agent, for example, fatty alcohol sulphates, alkyl aryl sulphonates, fatty acid condensation products, or polyoxyethylene compounds, and finally, if desired, other additives.

For the preparation of miscible oils the active compound is dissolved in a suitable solvent which preferably is poorly water-miscible, and one or more emulsifiers are added to this solution. Suitable solvents are, for example, xylene, toluene, petroleum distillates which are rich in aromates, for example, solvent naphtha, distilled tar oil and mixtures of these liquids. As emulsifiers may be used, for example, polyoxyethylene compounds and/or alkyl aryl sulphonates. The concentration of the active compound in these miscible oils is not restricted to narrow limits and may vary, for example, between 2 and 50% by weight. In addition to a miscible oil may also be mentioned as a liquid and highly concentrated primary composition a solution of the active substance in a readily water-miscible liquid, for example, a glycol, a glycol ether, dimethylformamide, or N-methylpyrrolidone, to which solution a dispersing agent, and if desired, a surface-active substance has been added. When diluting with water shortly before or during spraying, an aqueous dispersion of the active substance is then obtained.

An aerosol composition according to the invention is obtained in the usual manner by incorporation the active substance, if desired in a solvent, in a volatile liquid to be used as a propellant, for example, a mixture of chlorine-fluorine derivatives of methane and ethane, a mixture of lower hydrocarbons, dimethyl ether, or gases such as carbon dioxide, nitrogen and nitrous oxide.

Fumigating candles or fumigating powders, i.e. compositions which, while burning, can generate a pesticidal smoke, are obtained by taking up the active substance in a combustible mixture which may contain as a fuel a sugar or a wood, preferably in a ground form, a substance to maintain combustion, for example, ammonium nitrate or potassium chlorate, and furthermore a substance to delay combustion, for example, kaolin, bentonite and/or colloidal silicic acid.

In addition to the above-mentioned ingredients, the agents according to the invention may also contain other substances known for use in this type of agents. For example a lubricant, e.g., calcium stearate or magnesium stearate, may be added to a dispersible powder or a mixture to be granulated. "Adhesives", for example, polyvinylalcohol, cellulose derivatives or other colloidal materials, such as casein, may also be added so as to improve the adhesion of the pesticide to the crop. Furthermore, a substance may be added to reduce the phytotoxicity of the active substance, carrier material or auxiliary substance, for example, wool fat or wool fatty alcohol.

Pesticidal compounds known per se may also be incorporated in the compositions according to the invention. As a result of this activity spectrum of the composition is widened and synergism may occur.

For use in such a combination composition are to be considered the following known insecticidal, acaricidal and fungicidal compounds:

Insectides, for example:
1. organic chlorine compounds, for example 6,7,8,9,10,10-hexachloro -1,5,5a,6,9a-hexahydro-6,9-methano-2,4,3-benzo[e]-3- oxide;
2. carbamates, for example, 2-dimethylamino-5,6-dimethylpyrimidin-4-yl dimethyl carbamate and 2-isopropoxyphenyl methylcarbamate;
3. di(m)ethylphosphates, for example, 2-chloro-2-diethylcarbamoyl-1-methylvinyl-, 2-methoxycarbonyl-1-methylvinyl-, 2-chloro-1-(2,4-dichlorophenyl)vinyl-, and 2-chloro-1-(2,4,5-trichlorophenyl)vinyl di(m)ethylphosphate;
4. 0,0-di(m)ethyl phosphorothioates, for example, O(S)-2-methylthioethyl-, S-2-ethylsulphinylethyl-, S-2-(1-methylcarbamoylethylthio) ethyl-, 0-4-bromo-2,5,dichlorophenyl-, 0-3,5,6-trichloro-2-pyridyl-, 0-2-isopropyl-6-methylpyrimidin-4-yl-, and 0-4-nitrophenyl 0,0-di(m)ethyl phosphorothioate;
5. 0,0-di(m)ethyl phosphorodithioates, for example, S-methylcarbamoylmethyl-, S-2-ethylthioethyl-, S-(3,4-dihydro-4-oxobenzo d]-1,2,3-triazin-3-ylmethyl S-1,2-di(ethoxycarbonyl)ethyl-, S-6-chloro-2-oxobenzoxazolin-3-ylmethyl-, and S-2,3-dihydro-5-methoxy-2-oxo-1,3,4-thiadiazol-3-methyl 0,0-di(m)ethylphosphorodithioate;
6. phosphonates, for example, dimethyl 2,2,2-trichloro-1-hydroxyethylphosphonate;
7. natural and synthetic pyrethroids;
8. amidines, for example, N'-(2-methyl-4-chlorophenyl)-N,N-dimethylformamidine;
9. microbial insecticides, such as *Bacillus thuringiensis*;
10. carbamoyl-oximes, such as S-methyl N-(methylcarbamoyloxy) thioacetamidate; and
11. other benzoylurea compounds, such as N-(2,6-difluorobenzoyl)-N'-(4- chlorophenyl)urea.

Acaricides, for example:
1. organic tin compounds, for example, tricyclohexyl tin hydroxide and di[tri-(2-methyl-2-phenylpropyl)tin-]oxide;
2. organic halogen compounds, for example isopropyl 4,4'-dibromobenzilate, 2,2,2-trichloro-1,1-di(4-chlorophenyl)ethanol and 2,4,5,4'-tetrachlorodiphenyl sulphone;
3. synthetic pyrethroids, and furthermore: 3-chloro-α-ethoxyimino-2,6-dimethoxybenzyl benzoate and 0,0-dimethyl S-methylcarbamoyl methyl phosphorothioate.

Fungicides, for example:
1. organic tin compounds, for example, triphenyl tin hydroxide and triphenyl tin acetate;
2. alkylene bisdithiocarbamates, for example, zinc ethylene bisdithiocarbamate and manganese ethylene bisdithiocarbamate;
3. 1-acyl- or 1-carbamoyl-N-benzimidazole (-2) carbamates and 1,2-bis (3-alkoxycarbonyl-2-thiureido)benzene;

and furthermore 2,4-dinitro-6-(2-octylphenylcrotonate); 1-[bis(dimethylamino)phosphoryl]-3-phenyl-5-amino-1,2,4-triazole; N-trichloromethylthiophthalimide; N-trichloromethylthiotetrahydrophthalimide; N-(1,1,2,2-tetrachloroethylthio)tetrahydrophthalimide; N-dichlorofluoromethylthio-N-phenyl-N,N'-dimethylsulfamide; tetrachloroisophthalonitrile; 2-(4'-thiazolyl)-benzimidazole; 5-butyl-2-ethylamino-6-methylpyrimidine-4-yl-dimethylsulfamate; 1-(4-chlorophenoxy)-3,3-dimethyl-1(1,2,4-triazole-1-yl)-2-butanone; α-(2-chlorophenyl)-α-(4-chlorophenyl)-5-pyrimidinemethanol; 1-(isopropylcarbamoyl)-3-(3,5-dichlorophenyl) hydantoin; N-(1,1,2,2-tetrachloroethylthio)-4-cyclohexene-1,2-carboximide; N-trichloromethylmercapto-4-cyclohexene-1,2-dicarboximide; N-tridecyl-2,6-dimethylmorpholine; metal salts of ethylphosphite; and N-(2,6-dimethylphenyl-N-methoxyacetyl)alanine methylester; or mixtures of these compounds.

The dosage of the insecticidal and acaricidal composition according to the invention desired for practical application will, of course, depend on various factors, for example, application area, selected active substance, composition form, nature and extent of the infection, and the weather conditions.

In general it holds that favourable results are achieved with a dosage which corresponds to 1 to 5,000 g of the active substance per hectare.

For the above-described "through-feeding" the active substance is mixed through the food in a quantity which is effective for insecticidal application.

The compounds to be used in the compositions according to the invention are novel substances which can be prepared in a manner known per se for related compounds.

For example the compounds can be prepared by reacting a substituted aniline of the general formula

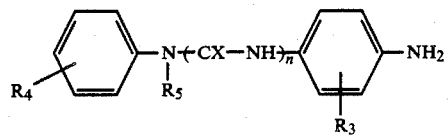

wherein $R_3$, $R_4$, $R_5$, n and X have the above meanings, with an isocyanate of the general formula

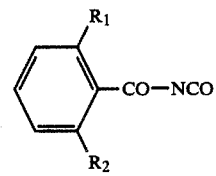

wherein $R_1$ and $R_2$ also have the above meanings. The new compounds can also be prepared by reacting a substituted benzamide of the general formula

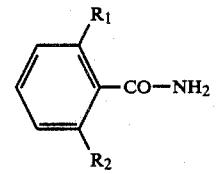

wherein $R_1$ and $R_2$ have the above meanings, with an isocyanate of the general formula

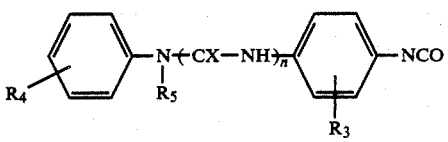

wherein $R_3$, $R_4$, $R_5$, n and X also have the above-mentioned meanings.

The above reactions are preferably carried out in the presence of an organic solvent, such as an aromatic hydrocarbon, an alkyl halide, a cyclic or non-cyclic dialkyl ether, or acetonitrile, at a reaction temperature between 0°C. and the boiling point of the solvent used. Although the above-indicated methods of preparing are the best suitable, the new compounds can also be prepared in a different manner, for example, as described in the above-mentioned Netherlands patent application 7105350 or according to the methods described in the Netherlands patent application Nos. 7806678 or 8005588. The invention will now be described in more detail with reference to the following specific examples.

EXAMPLE I

Preparation of N-(2,6-difluorobenzoyl)-N'-[4-{N-(4-chlorophenyl)-N-propylamino}phenyl]urea(4)

0.90 g of 2,6-difluorobenzoylisocyanate was added to a solution of 1.27 g of 4-[N-(4-chlorophenyl)-N-propylamino]aniline in 15 ml of dry diethylether while stirring at room temperature. After 1.5 hours at room temperature the formed precipitate was sucked off, washed with acetonitrile and diethylether, and dried. The desired product was obtained in a yield of 1.50 g; melting-point 169°–169.5°C. The starting aniline was obtained from the corresponding nitro compound by reduction with hydrogen under the influence of Raney nickel as a catalyst; a mixture of equal parts by volume of ethanol and ethyl acetate was used as a solvent. 1-Nitro-4-[N-(4-chlorophenyl)-N-propylamino]benzene was prepared by an alkylation of 1-nitro-4-(4-chloroanilino) benzene with propyliodide in dimethylformamide as a solvent under the influence of KOH, 1-Nitro-4-(4-chloroanilino) benzene was formed by a coupling at high temperature of p-chlorobenzeneisocyanate and p-nitrophenyl in nitrobenzene as a solvent. In a corresponding manner, in which, if desired, instead of diethylether acetonitrile was used as a solvent for the urea-formation, the following compounds were prepared; the compound numbers correspond with the numbers given before in the specification:

| compound no. | melting point | compound no. | melting point |
| --- | --- | --- | --- |
| 1 | 162.5–165.5° C. | 20 | 216–217° C. |
| 2 | 175.5–178.5° C. | 21 | 128–129° C. |
| 3 | 156° C. | 22 | 149–150° C. |
| 5 | 186–187° C. | 23 | 190–191° C. |
| 9 | 197–201° C. | 24 | 190° C. |
| 10 | 150° C. (decomp.) | 25 | 155° C. |
| 11 | 206° C. | 26 | 170–171° C. |
| 12 | 188–188.5° C. | 27 | 181–183° C. |
| 13 | 196–197° C. | 28 | 194–197° C. |
| 14 | 121.5–123.5° C. | 29 | 157–161° C. |
| 15 | 147–150.5° C. | 30 | 161–162° C. |
| 16 | 147.5–149.5° C. | 31 | 198–201° C. |
| 17 | 137–139° C. | 32 | 205–206° C. |
| 18 | 211.5–214.5° C. | 33 | 188–190° C. |
| 19 | 196–197° C. | | |

EXAMPLE II

Preparation of N-(2-chlorobenzoyl)-N'-[4-{N'-(4-chlorophenyl)-N'-propylureido}phenyl]urea (7)

1.09 g of 2-chlorobenzoylisocyanate was added to a solution of 2.00 g of N-(4-aminophenyl)-N'-(4-chlorophenyl)-N'-propylurea in 50 ml of acetonitrile while stirring at room temperature. After stirring for 1.5 hours at room temperature the formed precipitate was sucked off, washed with diethyl ether, and dried. According to PMR the product had the desired structure; the product melted at 170° C. The starting aniline was obtained from the corresponding nitro compound by reduction with hydrogen under the influence of Raney nickel as a catalyst; in this reaction ethanol was used as a solvent. N-(4-nitrophenyl)-N'-(4-chlorophenyl)-N'-propylurea was prepared by a coupling of p-nitrophenylisocyanate with N-propyl-4-chloroaniline in acetonitrile as a solvent. In a corresponding manner, in which, if desired, instead of acetonitrile diethyl ether was used as a solvent for the first-mentioned reaction, the following compounds were prepared; the compound numbers corresponding again with the numbers given before in the specification:

| compound no. | melting point | compound no. | melting point |
| --- | --- | --- | --- |
| 6 | 191–194° C. | 54 | 170–171° C. |
| 8 | 160° C. | 55 | 185° C. |
| 34 | 168–170° C. | 56 | 195–196° C. |

-continued

| compound no. | melting point | compound no. | melting point |
| --- | --- | --- | --- |
| 35 | 201–205° C. | 57 | 210° C. |
| 36 | 168–168.5° C. | 58 | 198–199° C. |
| 37 | 186–187° C. | 59 | 190–192° C. |
| 38 | 163–164° C. | 60 | 145° C. |
| 39 | 162–164° C. | 61 | 147° C. |
| 40 | 160–161° C. | 62 | 176–177° C. |
| 41 | >240° C. | 63 | 147–148° C. |
| 42 | 182–183° C. | 64 | 165–167° C. |
| 43 | 179–180° C. | 65 | 168–170° C. |
| 44 | 158–159° C. | 66 | 187–189° C. |
| 45 | 137–141° C. | 67 | 216–218° C. |
| 46 | 184–186° C. | 68 | 171–172° C. |
| 47 | 185–186° C. | 69 | 229–230° C. |
| 48 | 168–169° C. | 70 | 154–156° C. |
| 49 | 183–184° C. | 71 | >200° C. |
| 50 | 198–199° C. | 72 | 185–186° C. |
| 51 | 204–205° C. | 73 | 166–167° C. |
| 52 | 166–167° C. | 74 | 147–149° C. |
| 53 | 184–185° C. | | |

EXAMPLE III (a) Preparation of a solution of an active substance, viz. N-(2,6-difluorobenzoyl)-N'-[4-{N-(4-chlorophenyl)-N-propylamino}phenyl]urea, in a water-miscible liquid 10 g of the above active substance were dissolved in a mixture of 10 ml of isophorone and approximately 70 ml of dimethylformamide, after which polyoxyethylene glycol ricinyl ether was added as an emulsifier in a quantity of 10 g.

In a corresponding manner the other active substances were processed to 10 or 20% "liquids".

In corresponding manner "liquids" were obtained in N-methylpyrrolidone, dimethylformamide, and a mixture of N-methylpyrrolidone and isophorone as solvents.

(b) Preparation of a solution of the active substance in an organic solvent 200 mg of the active substance to be tested were dissolved in 1,000 ml of acetone in the presence of 1.6 g of nonylphenylpolyoxyethylene. After pouring out into water this solution can be used as a spray liquid.

(c) Preparation of a emulsifiable concentrate of the active substance 10 g of the active substance to be tested were dissolved in a mixture of 15 ml of isophorone and 70 ml of xylene; 5 g of a mixture of polyoxyethylene sorbitan ester and an alkyl benzene sulphonate as an emulsifier were added to this solution.

(d) Preparation of a dispersible powder (W.P.) of the active substance 25 g of the active substance to be investigated were mixed with 68 g of the kaolin in the presence of 2 g of sodium butylnaphthalene sulphonate and 5 g of lignine sulphonate.

(e) Preparation of a suspension concentrate (flowable) of the active substance

A mixture of 10 g of active substance, 2 g of lignine sulphonate and 0.8 g of sodium alkylsulphate were supplied with water till a total amount of 100 ml.

(f) Preparation of a granule of the active substance 7.5 g of active substance, 5 g of sulphite lye and 87.5 g of ground dolomite were mixed, after which the resulting mixture was processed to a granular composition by means of the so-called compacting method.

EXAMPLE IV

Young Brussels sprouts plants, approximately 15 cm high, were sprayed till run-off with compositions obtained according to Example III(b) in various concentrations; to these compositions had been added in addition approximately 250 mg of an alkylated phenol polyoxyethylene compound (Citowett) per liter. After the plants had dried, they were placed in cylinders of plexiglass and then infected with 5 larvae of *Pieris brassicae* (cabbage white butterfly) in the third larval stage (L3). The cylinders were then covered with a gauze and stored, an alternating light-dark cycle of 16 hours light and 8 hours dark being used; temperature in the light 24° C., rel. humidity (RH) 70%; temperature in the dark 19° C. 80–90% RH. After 5 days the mortality percentage of the larvae was established. Each experiment was carried out in triplicate. The average results of the experiments are recorded in Table A below. The meaning of the symbols in the table are as follows:

+ = 90–100% mortality
± = 50–90% mortality
− = <50% mortality

TABLE A

Insecticidal activity against larvae (L3) of *Pieris brassicae*

| compound no. | concentration in mg of act. ingred. per liter | | | | | | | |
|---|---|---|---|---|---|---|---|---|
| | 300 | 100 | 30 | 10 | 3 | 1 | 0,3 | 0,1 |
| 2 | + | + | + | + | + | + | − | |
| 4 | + | + | + | + | + | + | ± | − |
| 5 | + | + | + | + | + | + | − | |
| 11 | + | + | + | + | + | + | ± | − |
| 12 | + | + | + | + | + | + | − | |
| 13 | + | + | + | + | + | + | + | − |
| 15 | + | + | + | + | + | ± | − | |
| 18 | + | + | + | + | + | + | − | |
| 24 | + | + | + | + | + | + | − | |
| 35 | + | + | + | + | + | + | − | |
| 44 | + | + | + | + | + | + | − | |

Liquid insecticidal compositions are used in practice in quantities of approximately 1,000 liters per hectare. The coverage of the plants with the composition, however, is considerably less good in practice than in laboratory or glasshouse experiment as described hereinbefore. It has hence been found that in practive the dose is to be increased by factor 10 to obtain the same efficiency.

So in practical applications the above quantities with insecticidal activity correspond to approximately 4 to approximately 3,000 g of active substance per hectare.

EXAMPLE V

The growth tops of the broad beans were removed in such a way that four well developed leaves remained. The plants were sprayed till run-off with compositions obtained according to Example III(b) in various concentrations; to these compositions had moreover been added approximately 250 mg of Citowett per litre. After the plants had dried, they were placed in perspex cylinders and then infected with 5 larvae of *Spodoptera littoralis* (Egyptian cotton leafworm) in the third larval stage (L3). The cylinders were then covered with a gauze and stored as described in Example IV. After 5 days the mortality percentage of the larvae was established. Each experiment was carried out in triplicate. The average results of the experiments are recorded in table B.

The meanings of the symbols are the same as in Example IV.

TABLE B

Insecticidal activity against larvae (L3) of *Spodoptera littoralis*

| compound no. | concentration in mg of act. ingred. per liter | | | | | | |
|---|---|---|---|---|---|---|---|
| | 300 | 100 | 30 | 10 | 3 | 1 | 0,3 |
| 1 | + | + | + | ± | − | | |
| 2 | + | + | + | + | − | | |
| 3 | + | + | ± | ± | − | | |
| 4 | + | + | + | + | ± | − | |
| 5 | + | + | + | + | + | ± | − |
| 12 | + | + | + | + | + | ± | − |
| 13 | + | + | + | + | + | ± | − |
| 15 | + | + | + | + | ± | − | |
| 18 | + | + | + | ± | − | | |
| 19 | + | + | + | + | + | − | |
| 20 | + | + | + | + | + | − | |
| 21 | + | + | + | ± | − | | |
| 22 | + | + | + | + | ± | − | |
| 39 | + | + | + | + | − | | |
| 41 | + | + | + | ± | − | | |
| 45 | + | + | + | + | − | | |

In practice the above quantities with insecticidal activity correspond to approx. 10 to approx. 3,000 g of active substance per liter.

EXAMPLE VI

Dwarf French bean plants (*Phaseolus vulgaris*) having two well developed leaves were infected with *Tetranychus cinnabarinus* (carnation spider mite) by placing a given number of adult female mites on the plants. Two days after the infection the plants with the adult mites present thereon were sprayed till run-off with compositions obtained according to Example III(b) in various concentrations; to these compositions had moreover been added approximately 150 mg of an alkylated phenolpolyoxyethylene compound (Citowett) per liter. 5 Days after spraying, the adult insects were removed from the plants. The plants were stored for 2 weeks in a space with controlled temperature (T) and relative humidity (RH), an alternating light-dark cycle being used of 16 hours light and 8 hours dark. Light: T approximately 24° C., RH approximately 70%; dark: T approximately 19° C., RH 80–90%. The reduction of the population, i.e. the mortality of the larvae and eggs as compared with plants not treated with chemicals was established. The experiment was carried out in triplicate.

The average results if the experiments are recorded in Table C below. The meanings of the symbols used in the table are as follows:

+ = 90–100% reduction of the population; plants free or substantially free from spider mites;
± = 50–90% reduction of the population;
− = <50% reduction of the population, N-(2,6-difluorobenzoyl)-N'-(4-benzyloxyphenyl)urea (a), N-(2-chlorobenzoyl)-N'-[3,5-dichloro-4-(N-methyl-N-allyl)-aminophenyl]urea (b), N-(2,6-difluorobenzoyl)-N'-[3,5-dichloro-4-(N-methyl-N-allyl) aminophenyl]urea (c), N-(2-chlorobenzoyl)-N'-[4-(N-methyl-N-benzylimino)-phenyl]-urea (d) and N-(2,6-difluorobenzoyl)-N'-[4-(N-methyl-N-benzylimino)phenyl]urea (e) have been included in the tests by way of comparison.

TABLE C

Act. against *Tetranychus cinnabarinus* (carnation spider mite)

| compound no. | 300 | 100 | 30 | 10 | 3 | 1 | 0,3 |
|---|---|---|---|---|---|---|---|
| 1 | + | + | + | + | ± | − | |
| 2 | + | + | + | + | ± | − | |
| 3 | + | + | + | − | | | |
| 4 | + | + | + | + | + | − | |
| 5 | + | + | + | + | − | | |
| 6 | + | + | + | + | + | − | |
| 7 | + | + | + | + | + | ± | − |
| 8 | + | + | + | + | + | ± | − |
| 9 | + | + | + | ± | − | | |
| 11 | + | ± | − | | | | |
| 14 | + | + | + | − | | | |
| 15 | + | + | + | + | − | | |
| 16 | + | + | + | − | | | |
| 17 | + | + | + | − | | | |
| 18 | + | + | + | + | + | − | |
| 19 | + | + | ± | − | | | |
| 20 | + | + | + | + | − | | |
| 22 | + | + | + | ± | − | | |
| 23 | + | + | + | + | − | | |
| 24 | + | + | + | + | ± | − | |
| 25 | + | + | + | ± | − | | |
| 26 | + | + | + | + | − | | |
| 27 | + | + | + | − | | | |
| 28 | + | + | + | − | | | |
| 29 | + | ± | − | | | | |
| 30 | + | + | + | + | − | | |
| 31 | + | + | + | + | + | ± | − |
| 32 | + | − | | | | | |
| 33 | + | + | + | + | + | − | |
| 34 | + | + | + | + | ± | − | |
| 35 | + | + | + | + | + | − | |
| 36 | + | + | + | + | + | ± | − |
| 37 | + | + | + | + | + | ± | − |
| 38 | + | ± | − | | | | |
| 39 | + | − | | | | | |
| 40 | + | + | + | + | + | − | |
| 41 | + | + | + | + | + | − | |
| 42 | + | + | + | + | + | ± | − |
| 43 | + | + | + | + | + | − | |
| 44 | + | ± | − | | | | |
| 45 | + | + | + | − | | | |
| 46 | + | + | + | + | ± | − | |
| 47 | + | + | + | ± | − | | |
| 48 | + | + | + | + | + | − | |
| 49 | + | − | | | | | |
| 50 | + | + | + | + | + | + | − |
| 51 | + | + | + | + | + | − | |
| 52 | + | + | + | ± | − | | |
| 53 | + | + | + | ± | − | | |
| 54 | + | + | + | + | + | − | |
| 55 | + | + | + | + | + | − | |
| 56 | + | + | + | + | − | | |
| 57 | + | + | + | − | | | |
| 58 | + | + | + | + | ± | − | |
| 59 | + | + | + | + | ± | − | |
| 60 | + | + | + | + | + | − | |
| 61 | + | + | + | + | ± | − | |
| 62 | + | + | + | + | ± | − | |
| 63 | + | + | + | + | + | ± | − |
| 64 | + | + | + | + | + | ± | − |
| 65 | + | + | + | + | − | | |
| 66 | + | + | + | + | − | | |
| 67 | + | + | + | ± | − | | |
| 68 | + | + | + | + | − | | |
| 69 | + | + | + | + | − | | |
| 70 | + | + | + | + | − | | |
| 72 | + | + | + | − | | | |
| 73 | + | + | + | + | − | | |
| 74 | + | + | + | ± | − | | |
| a | − | | | | | | |
| b | − | | | | | | |
| c | − | | | | | | |
| d | − | | | | | | |
| e | − | | | | | | |

In practice the above quantities with acaricidal activity correspond with approx. 10 to approx. 3,000 grams of active substance per hectare. Repetitions of the above experiments, wherein the adult mites were removed prior to the spraying (method A), or wherein the spraying was carried out prior to the infection (method B), yielded about the same results.

EXAMPLE VII

In the same way as described in Example VI, method B, benzoylurea compounds according to the invention were tested on *Panonychus ulmi* (European red mite). The results are recorded in table D, wherein the symbols have the same meanings as in Example VI.

TABLE D

Activity against *Panonychus ulmi* (European red mite)

| compound no | 300 | 100 | 30 | 10 | 3 | 1 |
|---|---|---|---|---|---|---|
| 1 | + | + | + | + | + | − |
| 2 | + | + | + | − | | |
| 3 | + | + | + | + | ± | − |
| 4 | + | + | + | + | ± | − |
| 5 | + | + | + | ± | | |
| 6 | + | + | + | + | ± | − |
| 7 | + | + | + | + | + | ± |
| 8 | + | + | + | + | − | |
| 9 | + | + | + | + | + | ± |
| 11 | + | ± | − | | | |
| 12 | + | | | | | |
| 13 | + | | | | | |
| 14 | + | + | + | + | − | |
| 15 | ± | ± | − | | | |
| 16 | + | + | + | ± | − | |
| 17 | + | + | + | − | | |
| 18 | + | | | | | |

Liquid compositions are applied on fruit-trees in quantities of approx. 1,500 liters per hectare. Then the above quantities with acaricidal activity correspond in practice with approx. 45 to approx 4,500 grams of active substance per hectare.

EXAMPLE VIII

In the same way as described in Example VII, wherein, however, the spraying was carried out after infection of the plants (method A of Example VI), benzoylurea compounds according to the invention were tested on *Panonychus ulmi* (European red mite). The results are recorded in table E, wherein the symbols have the same meanings as in Example VI.

TABLE E

Activity against *Panonychus ulmi* (European red mite)

| compound no. | 300 | 100 | 30 | 10 | 3 | 1 |
|---|---|---|---|---|---|---|
| 1 | + | + | + | + | + | ± |
| 2 | + | + | + | + | ± | − |
| 3 | + | + | + | ± | − | |
| 4 | + | + | + | − | | |
| 5 | + | + | + | − | | |
| 6 | + | + | + | + | + | − |
| 7 | + | + | + | + | + | + |
| 8 | + | + | + | + | − | |
| 9 | + | + | + | + | + | − |
| 11 | + | ± | − | | | |
| 12 | + | + | + | + | − | |
| 13 | + | + | + | + | ± | |
| 14 | + | + | + | ± | − | |
| 15 | + | + | + | ± | − | |
| 16 | + | + | + | + | − | |
| 17 | + | + | + | − | | |
| 18 | + | + | + | + | + | ± |
| 19 | + | + | ± | − | | |
| 20 | + | + | + | − | | |
| 21 | + | + | + | − | | |
| 22 | + | + | + | ± | − | |

TABLE E-continued

Activity against *Panonychus ulmi* (European red mite)

| compound no. | concentration in mg of act. ingred. per liter. | | | | | |
|---|---|---|---|---|---|---|
| | 300 | 100 | 30 | 10 | 3 | 1 |
| 23 | + | + | + | + | − | |
| 24 | + | + | + | − | | |
| 25 | + | + | + | + | + | − |
| 26 | + | + | + | + | ± | − |
| 27 | + | + | + | + | − | |
| 28 | + | + | + | + | − | |
| 29 | + | ± | − | | | |
| 30 | + | + | + | + | − | |
| 31 | + | + | + | + | | |
| 32 | + | ± | − | | | |
| 33 | + | + | + | + | − | |
| 34 | + | + | ± | − | | |
| 36 | + | + | + | + | − | |
| 37 | + | + | + | + | − | |
| 40 | + | + | + | + | − | |
| 41 | + | + | + | ± | − | |
| 42 | + | + | + | + | − | |
| 43 | + | + | + | ± | − | |
| 46 | + | + | + | − | | |
| 48 | + | + | + | − | | |
| 49 | + | ± | − | | | |
| 50 | + | + | + | + | − | |
| 51 | + | + | + | ± | − | |
| 52 | + | ± | ± | − | | |
| 53 | + | + | + | − | | |
| 54 | + | + | + | − | | |
| 55 | + | + | + | ± | − | |
| 56 | + | + | − | | | |
| 58 | + | + | + | ± | − | |
| 59 | + | + | + | + | − | |
| 60 | + | + | + | + | − | |
| 61 | + | + | + | + | − | |
| 62 | + | + | + | + | − | |
| 63 | + | + | + | + | + | − |
| 64 | + | + | + | + | + | − |
| 65 | + | + | + | ± | − | |
| 66 | + | + | ± | − | | |
| 68 | + | + | + | + | − | |
| 72 | + | + | + | | | |
| 73 | + | | | | | |
| 74 | + | + | + | | | |

What is claimed is:

1. A composition having insecticidal and acaricidal activity, comprising a liquid or solid inert carrier material and an active substance of the formula.

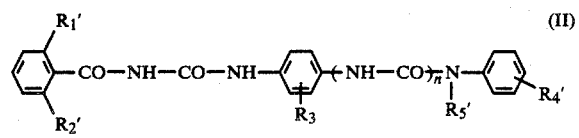

wherein $R_1'$ and $R_2'$ are both fluorine atoms, or wherein $R_1'$ is a chlorine atom and $R_2'$ is a hydrogen atom, $R_3$ is a hydrogen atom or represents 1 or 2 substituents which are selected from the group consisting of halogen, methyl and trifluoromethyl, $R_4'$ is a hydrogen atom or represents 1–3 substitutents which are selected from the group consisting of halogen, $C_1$–$C_4$ alkyl, $C_1$–$C_4$ haloalkyl and $C_1$–$C_4$ haloalkoxy, n is 0 or 1, and $R_5'$ is a hydrogen atom or a $C_2$–$C_5$ alkyl group, with the proviso, that, if n is 0 and $R_5'$ is a hydrogen atom, $R_3$ is a hydrogen atom.

2. A composition as claimed in claim 1, wherein the active substance is a compound selected from the group consisting of:
N-(2-chlorobenzoyl)-N'-[4-{N-(4-chlorophenyl)-N-ethylamino}phenyl]urea,
N-(2-chlorobenzoyl)-N'-[4-{N'-(4-chlorophenyl)-N'-isopropylureido}phenyl]urea,
N-(2-chlorobenzoyl)-N'-[4-{N'-(4-chlorophenyl)-N'-propylureido}phenyl]urea, and
N-(2-chlorobenzoyl)-N'-[4-(4-chloroanilino)phenyl-]urea.

3. A method of controlling insects and mites, wherein the infected area is treated with a composition as claimed in claim 1 in a dosage of 1 to 5000 grams of active substance per hectare.

* * * * *